United States Patent [19]

Maines

[11] Patent Number: 4,710,458

[45] Date of Patent: * Dec. 1, 1987

[54] NYLON STRIPS FOR MEDICAL ASSAY

[75] Inventor: Robert Maines, Tappan, N.Y.

[73] Assignee: R. J. Harvey Instrument Corporation, Hillsdale, N.J.

[ * ] Notice: The portion of the term of this patent subsequent to Jul. 1, 2003 has been disclaimed.

[21] Appl. No.: 257,860

[22] Filed: Apr. 27, 1981

Related U.S. Application Data

[63] Continuation-in-part of Ser. No. 76,222, Sep. 17, 1979, Pat. No. 4,279,506.

[51] Int. Cl.$^4$ .................. C12Q 1/00; C12Q 1/28; C12Q 1/54
[52] U.S. Cl. ........................... 435/12; 422/56; 435/14; 435/19; 435/25; 435/28; 435/805
[58] Field of Search ............... 422/55, 56, 57; 435/4, 435/805, 14, 12, 19, 25, 28; 436/172

[56] References Cited

U.S. PATENT DOCUMENTS

| | | | |
|---|---|---|---|
| 3,298,789 | 1/1967 | Mast | 435/14 |
| 3,897,214 | 7/1975 | Lange et al. | 435/805 X |
| 3,992,631 | 11/1976 | Harte | 436/172 X |
| 4,029,598 | 6/1977 | Neisius et al. | 422/56 X |
| 4,050,898 | 9/1977 | Goffe et al. | 422/57 |

OTHER PUBLICATIONS

Werner et al., Clin. Chem. 25/1, 20–23(1979).

Campbell et al., Biochimica et Biophysica Acta, 384(1975)307–316.

*The Condensed Chemical Dictionary*, Revised by Gessner G. Hawley, 8th Edition, Van Nostrand Reinhold Company, New York, 1971, p. 635.

*Primary Examiner*—Arnold Turk

[57] ABSTRACT

Photometric apparatus, for counting the particulate components in blood and for determining the degree of particulate agglutination is disclosed. The apparatus comprises a body provided with an absorbent well for holding the blood bearing solution. The body is further provided with a passage to allow communication between the well and a detector which is capable of detecting the response of the particulate material to stimulating radiation. The absorptive well has the characteristic of absorbing radiation at the wavelength which characterizes the response of the particulate material to stimulating radiation. The well advantageously prevents the detector from detecting radiation that would otherwise be reflected by the well, whereby the linearity of the response of the apparatus is greatly increased. Linearity is further enhanced by assuring full crenation of the cells with a specific reagent. Impregnation of the well walls with specific reagents and/or enzymes, such that the addition of water or solution will result in a working test solution for a variety of blood serum or urine analysis is further disclosed. Test strips impregnated with specific reagents and enzymes, which are adapted to produce a permanent record of the test color intensity, are also disclosed.

4 Claims, 4 Drawing Figures

NYLON STRIPS FOR MEDICAL ASSAY

This application is a continuation-in-part of U.S. patent application, Ser. No. 076,222, filed on Sept. 17, 1979 now U.S. Pat. No. 4,279,506.

FIELD OF THE INVENTION

This invention relates to the method and apparatus for quantizing various whole blood components and conducting other turbinometric and nepholimetric tests

BACKGROUND OF THE INVENTION

Commercially available automated equipment currently exists for analyzing the particulate or cell concentration in blood. This equipment measures either the interaction of the blood particles with electric fields or the interaction of the blood particles with visible radiation. Instruments which utilize electric fields for blood analysis require rather complex equipment while instruments utilizing optical analysis techniques are simpler. However, the simplicity found with optical instruments is frequently obtained at the expense of accuracy.

A disadvantage of utilizing optical equipment to analyze the particulate concentration in blood is the fact that the visible radiation intensity used to determine particulate concentration does not vary linearly with changes in particulate concentration. This is due to the fact that instruments using nephelometric and/or turbinometric phenomenon have non-linear characteristics as a result of random scattering of light. The non-linear response of the optical equipment to the particulate concentration makes the interpretation of the output data difficult and somewhat inaccurate. If instrumentation is added to the optical equipment to linearize its response, its complexity rapidly approaches that of the electric field instruments. Thus, a highly desirable goal in blood analysis is to develop a simple optical instrument not requiring elaborate instrumentation, which responds linearly to changes in particulate concentration.

Moreover, in the past it has been necessary, when conducting these types of tests to separately mix the required test reagents with the test sample, thereby substantially increasing both the time necessary to complete the test and the chance of contaminating the sample. In order to overcome these shortcomings, attempts have been made to produce a test strip or vessel impregnated with the actual test reagents. However, these products have proved unsatisfactory for a number of reasons. The first is that in many cases it has been difficult, if not impossible, to adapt the vessel and/or strip material to absorb and hold, in a stable condition, the necessary test reagents, dyes, or enzymes. Secondly, due to the type of dyes either used or generated, as well as the fact that these dyes are not molecularly bonded to the vessel or strip material, they do not result in a stable and permanent color. Rather, these tests must be read during a relatively short period of time after the test reaction is complete.

It is therefore an object of this invention to provide simple optical equipment for automatically analyzing the particulate content in blood bearing solutions.

It is another object of this invention to provide optical equipment capable of simultaneously analyzing and detecting two constituents in blood bearing solutions.

It is a further object of this invention to provide an instrument capable of obtaining a linear reading of the degree of agglutination of red blood cells.

A still further object of this invention is to provide a technique for increasing the linearity of response of optical equipment used to determine the particulate concentration in whole blood and in other solutions.

A further object of this invention is to provide a vessel adapted to absorb a number of various test reagents and enzymes which will be leached out when the test sample is added thereto.

Another object of this invention is to provide a test strip impregnated with various test reagents adapted to indicate specific analyte concentration by means of changes in color.

Still, a further object of this invention is to provide a test strip which will produce a permanent record of test results.

Still, other objects and advantages of the present invention will be obvious and in part be apparent from the specification and attached drawings

SUMMARY OF THE INVENTION

In accordance with one aspect of the invention the particulate components in whole blood are counted and the degree of agglutination is determined by an apparatus which detects the concentration or rate of change of concentration of particles, and/or other material, exhibiting a visible spectrum response to interactive radiation. The interactive radiation may be visible light, or radiation from radioactive sources, and may either be externally or internally generated. A transparent envelope containing a blood bearing solution is subjected to the interactive radiation and the envelope is surrounded by a broadly absorbent body having a central internal cavity accommodating and supporting the transparent envelope. The broadly absorbent body having a relatively restrictive passage, allows visual communication between the internal cavity and the exterior thereof. A detector having an electrical signal output and capable of detecting at least a portion of the responsive visible radiation spectrum is positioned to detect the responsive radiation communicated via the relatively restrictive passage.

It is a feature of the invention that the broadly absorbent body strongly absorbs radiation at the responsive visible radiation wavelength, thereby eliminating the effects of radiation scattering from the wall of the well and advantageously increasing the linearity of the detector response.

In accordance with a second aspect of the invention multiple externally generated radiation sources are utilized to achieve simultaneous visible spectrum responses from at least two components of the blood. A transparent envelope contains the solution bearing the particulate components of blood and this envelope is surrounded by a broadly absorbent body having an internal cavity of size sufficient to accommodate and support the envelope. The broadly absorbent body has four coplanar relatively restrictive passages communicating between the internal cavity of the body and the exterior thereof. First and second passages have aligned axes extending in opposite directions from the cavity and third and fourth passages have aligned axes coplanar with said first and second passages which also extend in opposite directions from the cavity. Located externally to the body are two detectors with electrical signal outputs, a first of which is positioned to receive radiation via the second passage, while a second detector is positioned to receive radiation via the fourth passage, each detector capable of detecting at least a portion of the responsive radiation spectrum.

It is another feature of the invention that each particle to be counted absorbs and/or scatters radiation at the wavelength of only one of the external radiation sources and each detector is responsive to only one of the external radiation sources, whereby each detector measures the concentration of a particular particle.

In accordance with a third aspect and feature of the invention linearity and stability of response of visible radiation to the particle concentration in whole blood is enhanced by crenating the red blood cells with a specific reagent and by refractively matching the red cell membranes to the reagent.

In accordance with another aspect and feature of the invention, the well of the apparatus is impregnated with a test reagent and/or enzyme and dried. Upon addition of water or a sample solution, the reagent and/or enzyme is leached out of the impregnated material of the well, resulting in a working test reagent. As with most tests of this nature, a quantitative determination of the analyte present may be made by monitoring the intensity of the resulting color in accordance with the previously discussed features of the invention.

In accordance with still a further aspect of the invention, a strip made in accordance with the material used in the construction of the above-mentioned well is impregnated with enzymes and/or other reagent constituents. Upon dipping the test strip into the solution to be tested, the strip will absorb the test solution, thereby reacting with the reagents impregnated therein. This reaction will result in a color being generated, the intensity of which is related to the concentration of the analyte for which the test is being conducted. The test strip may then be subjected to a visual or instrument evaluation which will quantitatively measure the intensity of the color.

The foregoing and other objects and features of this invention will be more fully understood from the following description of an illustrated embodiment thereof taken in conjunction with the accompanying drawings

DETAILED DESCRIPTION

Figure 1:
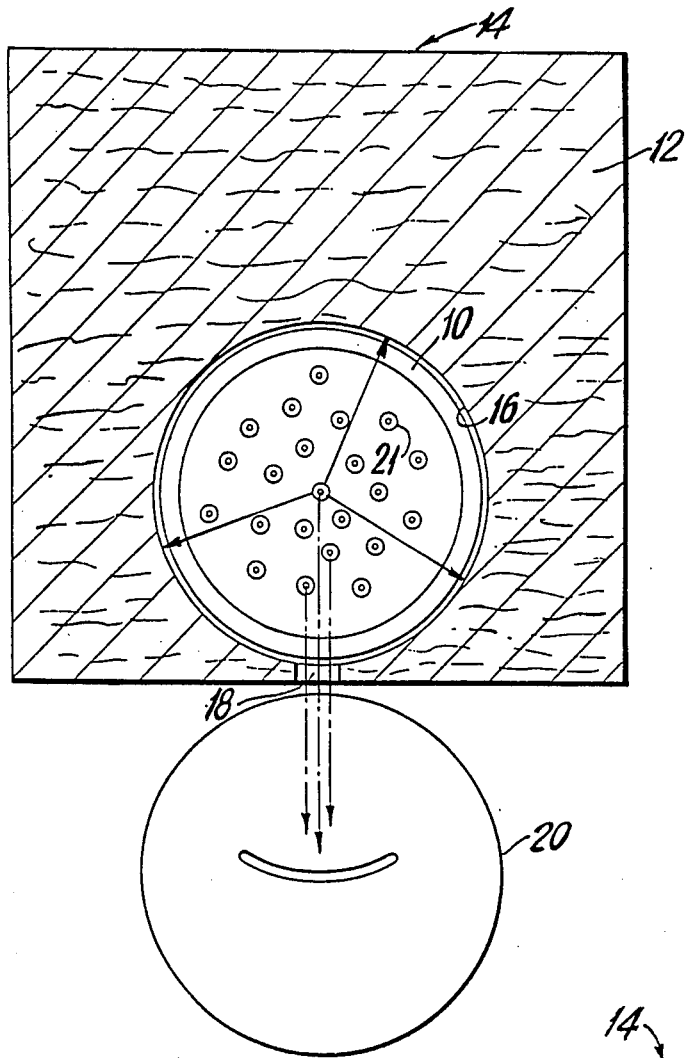
FIG. 1 is a top sectional view of a counting chamber where the detected radiation results from radioactive decay of isotopes added to the solution.

Referring to FIG. 1 there is shown a first embodiment of the invention. A transparent cuvette or envelope 10 is surrounded with and supported by a rectangular body or well 12, the well having an exterior surface 14 and a centrally located internal cavity 16. The internal cavity 16 is carefully sized such that it is large enough to accommodate the envelope 10 but small enough to provide adequate support therefor. Rectangular body or well 12 has a relatively restrictive passage 18 communicating between the internal cavity 16 and the exterior surface 14 of the rectangular body or well 12. A photomultiplier detector 20 is positioned to intersect the path of the relatively restrictive passage, thereby receiving any radiation transmitted via the restrictive passage 18.

It is noted that although the body of the apparatus is depicted as being rectangular and the well circular, it is understood that the invention is not so limited in that both the body and well may take on a number of various shapes and sizes to accommodate not only the type of test being conducted, but also the amount of test sample being used.

A measured quantity of liquid, including material which contains a radioactive isotope such as $C_{14}$, is placed in the cuvette 10. Also included in the liquid is material capable of fluorescence in response to the radioactive isotope. The $C_{14}$ generates a characteristic radiation which excites the fluorescent material in the liquid and causes it to fluoresce at wavelengths between 380 nm and 420 nm. This radiation is transmitted via the relatively restrictive passage 18 to photomultiplier detector 20. Detector 20 detects the radiation generated by the particles in the solution and, in response thereto, the detector produces an electrical output signal. The magnitude of the electrical output signal is proportional to the concentration of $C_{14}$ and also is proportional to the concentration of the material containing $C_{14}$, and this signal output can be utilized in a well known manner to operate display devices for indicating the material concentration. The material can be red blood cells or any other organic material capable of being tagged with $C_{14}$.

The material contained within the cuvette 10 such as material 21 is not limited to cell particles but is meant to indicate any material containing $C_{14}$ which excites the fluorescent material in the liquid.

An important aspect of the invention is the fact that broadly absorbent well 12 is advantageously constructed of a material, which when dyed, will strongly absorb radiation in the wavelengths from 340 to 640 nm. Therefore, all radiation sensed by detector 20 consists of radiation generated by the excited material in the liquid and does not consist of secondary radiation caused by reflection of the transmitted radiation from the sides of well 12. The lack of reflected radiation is due to the fact that well 12 has been constructed of a material which strongly absorbs radiation at the wavelength of the radiation being generated by the excited material. This is in marked contrast to prior art devices which utilize a non-absorbent well which causes scattering of the generated radiation. This scattering or reflection off the walls of the well results in the detector response being partially due to a reflected component of radiation, thereby causing undesirable non-linearity in the detector output. Using an absorbent well having an absorption band that matches the wavelength of the light sensed by the detector ensures that the resulting detector response will entirely be a function of the first order light generated by the excited material, and thus the detector output signal will vary linearly with $C_{14}$ concentration.

A well 12, broadly absorbent of radiation, can be made from a cast or molded of a material such as Nylon IV, which can be produced in accordance with the teachings set forth in U.S. Pat. Nos. 3,174,951 and 3,721,625. Nylon IV can be dyed with commercially available dyes to make Nylon IV strongly absorbent of radiation across the entire visible spectrum and the ultraviolet spectrum. More particularly, to make Nylon IV strongly absorbent across a broad range of wavelengths, the Nylon IV can be dyed with commercially available dyes obtainable from Crompton and Knowles Corporation of Reading, PA. or Barson Corporation of Stamford, Conn. Examples of dyes utilized to make the Nylon IV absorbent from 340 nm to 640 nm include the following: Altco Fast Black, Super Nylite Black 40R, Intralow Black BGL, Nylonthrene Black GLRT, Azoanthrene Jet Black K, Direct Black E and Intrachrome Black WA.

Procedures recommended by Crompton and Knowles and/or Barson are utilized to dye the Nylon IV. These dyeing procedures are supplied by Crompton and Knowles and/or Barson, along with the appropriate dyes. Dyeing the Nylon IV well material in accordance with these teachings ensures that the well material will be strongly absorbent at the visible and ultraviolet wavelengths, and thus all radiation collected by detector 20 will be radiation stemming from the excited particles in the solution and will not be radiation reflected from the walls of well 12.

Figure 2:
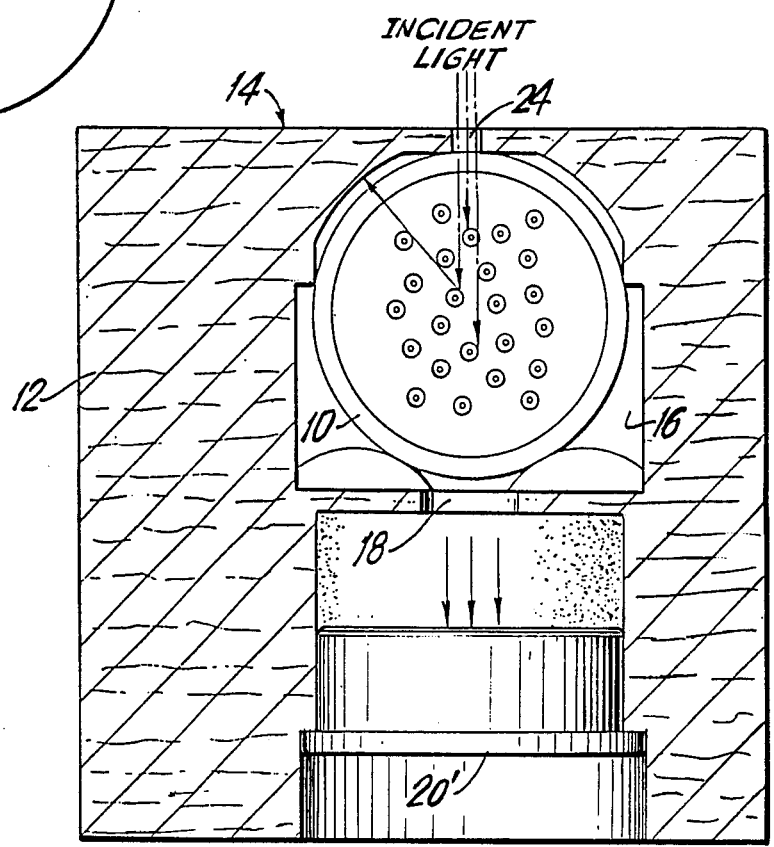
FIG. 2 is a top sectional view of a counting chamber where the incident radiation is generated by a single monochromatic external source and the measured radiation is the transmitted radiation.

FIG. 2 illustrates a second embodiment of the invention. The apparatus shown therein consists of a transparent cuvette or envelope 10 surrounded by a rectangular body or well 12, having an exterior surface 14 and a centrally located internal cavity 16. The central cavity 16 is carefully sized such that it is large enough to accommodate the envelope 10 but small enough to provide adequate support for the envelope 10. The well 12 of the present embodiment differs from the first embodiment in that it has two relatively restrictive passages rather than one relatively restrictive passage. The first relatively restrictive passage 24 communicates between the internal cavity 16 and the exterior surface 14 of the rectangular body or well 12. A second relatively restrictive passage 18, having a common axis with the first relatively restrictive passage 18, extends in the opposite direction from the central cavity 16 and communicates between the central cavity 16 and the surface 14.

Adjacent to exterior surface 14 of well 12 is a solid state detector 20' which is positioned to intersect the path of the first relatively restrictive passage 18 and is positioned so as to detect radiation transmitted through passage 18. Such solid state detectors are commercially available and could, for example, be a Hammatmatsu silicon photo-cell detector.

In this embodiment of the invention a measured quantity of a blood bearing solution having the particulate component randomly dispersed throughout is placed in the cuvette 10. An externally generated monochromatic light of a wavelength equal to 420, 540 or 578 nm is directed into the cavity via the first relatively restrictive passage 24. The monochromatic light passes through the cell membrane and is strongly absorbed by the oxyhemoglobin in the red cell and the number of particles in the light path is then directly proportional to the amount of light absorbed. The light transmitted through the solution is directed to solid states detector 20' via relatively restrictive passage 18. The intensity of the radiation received by detector 20' decreases as the concentration of the particles increases. Therefore, the detector output can readily be utilized to operate display devices for indicating the cell concentration of cells in whole blood.

Determining the concentration of cells in whole blood through use of an external radiation source as in FIG. 2 requires an additional consideration due to the shape of the cells. More particularly, blood cells are rather flat and transparent to light, and thus their response to the incident light will depend on the orientation of each cell with respect to the axis of the transmitted light and will also depend on the swirling motion of the cells within the solution. A more linear detector response to the transmitted light can be obtained by first crenating the blood cells with the proper reagent.

Full crenation of the cells is accomplished by adding about one part of whole blood to about 250 to 2000 parts of a hypertonic solution and preferably about one part of whole blood to about 300 to 750 parts solution. This hypertonic solution contains distilled water to which is added about 1% to 9% and preferably 2% to 4% by weight of a salt and from about 1% to 8% and preferably 4% to 6% by weight of a polysaccharide, wherein the total percentage of the salt and polysacride will be about 2% to 17% and preferably about 6% to 10%.

It has been found that a solution of one part whole blood and five hundred parts of a hypertonic solution which comprises distilled water to which has been added about 3% by weight of Sodium Benzoate and 6% by weight of dextran having an average molecular weight of about 200,000 to 300,000 performs satisfactorily. In addition, the above solutions may also contain from about 1% to about 4% by weight of a plasma expander, such as a poly vinyl perrolidone. The whole blood and the hypertonic solution are thoroughly mixed and the mixture is allowed to stand for a minimum of about one minute to ensure that the cells are fully crenated.

A solution having the above composition, in addition to preparing the red blood cells by crenation, also serves to provide a solution which has an index of refraction which approximately matches the index of refraction of the red blood membrane, and thus reduces the reflected light and enhances the linearity of the detector response. In addition, the effective total area of the concentrated red cell hemoprotein in the light path has to be small in comparison to the total area of the incident light beam. An appropriate ratio of hemoprotein area to light beam area is 1 to 10. Such a ratio is achieved by proper dilution of the solution and ensures that counting errors will not result as cell volume increases or decreases. This minimizes counting errors due to MCV (mean corpuscular volume) variations. This relationship must be utilized with the embodiment of FIG. 2 and the embodiment of FIG. 4 to be described hereinafter.

The body material of well 12 is again advantageously designed to be absorbent at the wavelength of the radiation transmitted by the external monochromatic light source. The specific material of which well 12 is constructed, and the manner in which this material is rendered absorbent at the wavelength of the monochromatic light source is in accordance with the teachings of U.S. Pat. Nos. 3,174,951 and 3,721,625 and the dyeing process described above. Since the body material of well 12 is absorbent at the wavelength of the transmitted radiation, the intensity of the measured radiation will vary linearly with respect to particle concentration and will not be affected by reflections from the walls of well 12 due to the fact that the well wall is absorbent.

Figure 3:
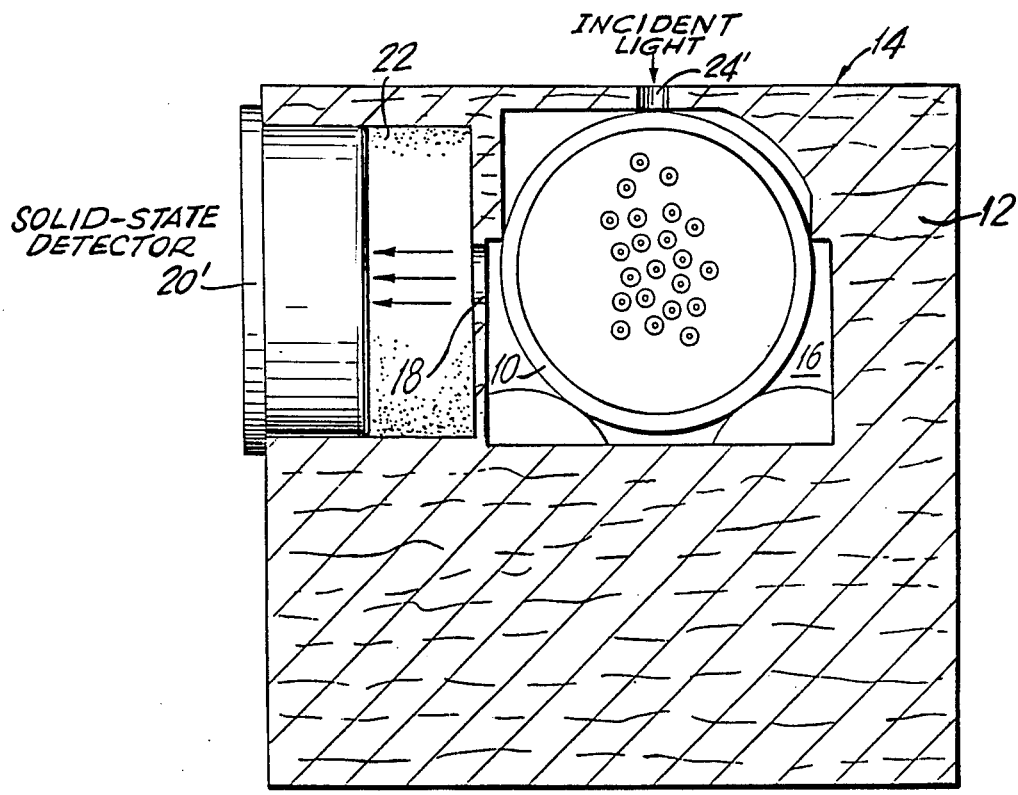
FIG. 3 is a top sectional view of a counting chamber where incident radiation from an external monochromatic source excites fluorescence by the particles, the fluorescence being measured.

FIG. 3 illustrates a third embodiment of the invention. The apparatus shown therein includes cuvette 10, internal body cavity 16, the selectively absorbent well 12 and an additional element not previously used, namely filter 22. This embodiment of the invention is contrasted with the previous embodiments in that the second relatively restrictive path 24' is perpendicular to the first relatively restrictive path 18 and extends from central cavity 16 to the surface 14. This apparatus is particularly well suited to an application wherein an externally generated monochromatic light source is employed to excite fluorescence in the species being studied. When employing a light source to excite fluorescence there is always the problem of having the detector differentiate between the light source and the radiation generated through fluorescence. Such differentiation is necessary if the detector output is to accurately reflect particle concentration. This problem is solved in the above-described configuration of restrictive passages due to the fact that passage 24' is perpendicular to passage 18, thereby ensuring that the detector is shielded from the direct beam of the external monochromatic light source. This feature enhances the linearity of the detector response, since all light incident on the detector is generated by the fluorescence originating from the solution. In addition, filters 22 are arranged to block radiation at the frequency of the incident light, thereby adding to the accuracy of the concentration readings. Examples of radiation wavelengths are 366 nm for the wavelength of the incident light and 450 nm for the wavelength of fluorescence.

Again, the material of well 12 is advantageously made strongly absorbent at the wavelengths of the fluoresced light and the incident light. This further increases the linearity of the detector response in accordance with the teachings outlined above. In this configuration the well material can be made absorbent at the wavelength of both the fluoresced light and the external light but absorbence should principally occur at the wavelength of the fluoresced light.

Figure 4:
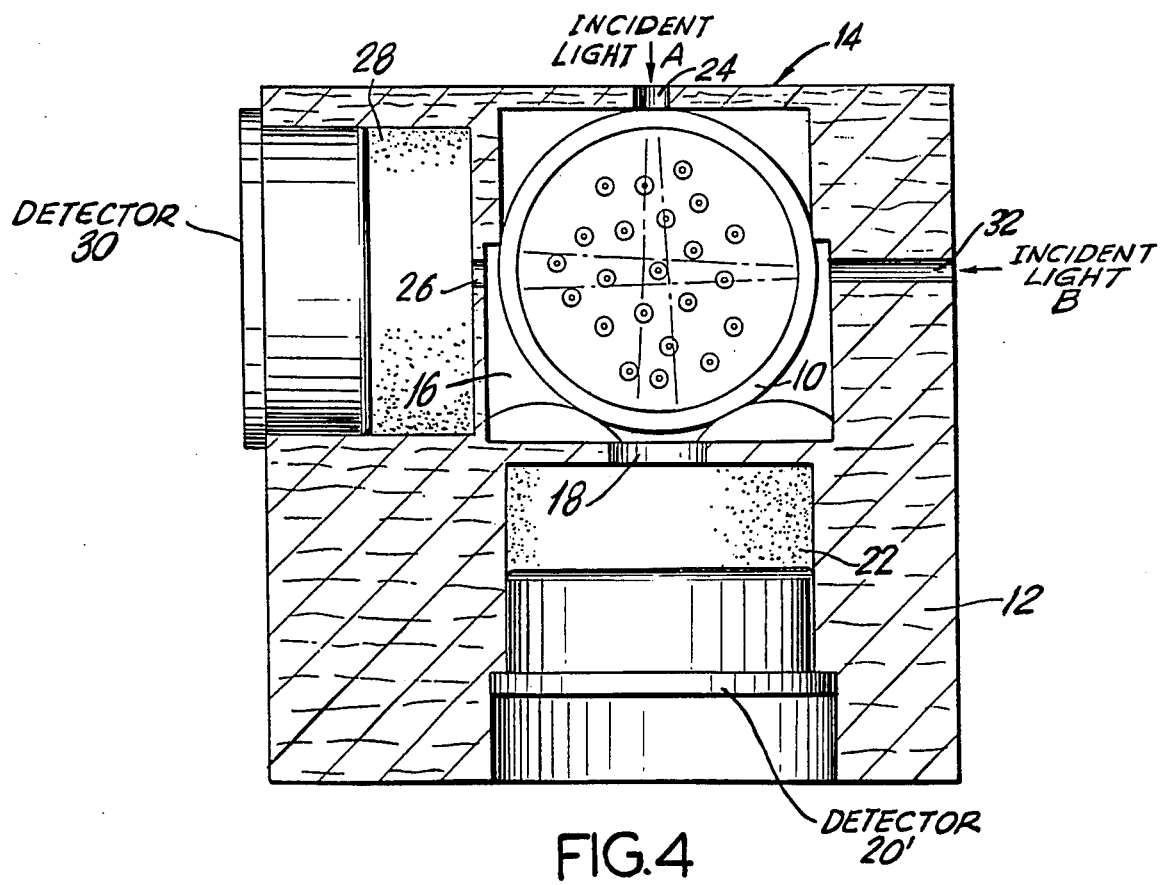
FIG. 4 is a top sectional view of a counting chamber where incident radiation is generated by two external monochromatic sources.

A fourth embodiment of the invention is shown in FIG. 4. This embodiment includes the structural elements defined above, namely, the absorptive well 12, the cuvette 10, body cavity 16 and filters 22. This embodiment differs from those described above in that it has a second pair of relatively restrictive passages 26 and 32 communicating between the central cavity 16 and the surface 14 of the well 12. Associated with third relatively restrictive passage 26 is a second series of filters 28 and a second solid state detector 30. The spacial radiation between the second series of filters 28, the second solid state detector 30, and the third relatively restrictive passage 26 is the same as the spacial relation between the first series of filters 22, solid state detector 20', and the first relatively restrictive passage 18. The fourth relatively restrictive passage 32 directs a second externally generated monochromatic light source into the central cavity 16.

The apparatus in FIG. 4 allows the simultaneous measurement of the concentration of two species in whole blood. More particularly, the white blood cell concentration and the platelet concentration can be measured simultaneously. This is accomplished by setting the wavelength of incident light source A at 420 nm and the wavelength of incident light source B at 460 nm. It is understood that prior to measuring the concentration of the white blood cells and platelets the red blood cells must be removed from solution, since these cells will detrimentally interfere with the reflection and absorption of the incident light sources used to determine the concentration of the white cells and platelets.

When the blood bearing solution has been treated with the reagent described above in relation with the crenation process and the red blood cells have been removed, the platelets in the blood reflect light at 420 nm and are completely transparent to the light at 460 nm. Therefore, the light from source A (420 nm) will be reflected by the platelets and absorbed by the well, and thus the output of detector 20' will reflect the platelet concentration. Similarly, the light from source B (460 nm) will be absorbed by the white blood cells and the output of detector 30 will reflect the white blood cell concentration. Filters 22 advantageously reject at 460 nm and filters 28 reject at 420 nm to further increase concentration measurement accuracy. Again, the material of well 12 is dyed in accordance with the teachings set forth above to be absorbent at 420 nm and 460 nm to thereby greatly increase the linearity and accuracy of the cell concentration readings.

All of the embodiments described above can also be used to determine the degree of agglutination of the red blood cells. More particularly, in accordance with the previous teachings it can be appreciated that the apparatus of the instant invention will provide an accurate reading of the number of red blood cells. As the red blood cells agglutinate together, this count will decrease at a specific rate based on the number of cells that combine together. Due to the enhanced linearity inherent in the apparatus of the instant invention the degree of agglutination can be accurately determined.

In another embodiment of the present invention the Nylon IV used to make the well portion of the apparatus is impregnated with one or more enzymes or reagents necessary to conduct a variety of tests on blood or urine samples. Although the remaining embodiments of the present invention will be discussed in terms of blood and/or urine testing, these are exemplary only and it should be understood that the present apparatus may be adapted to determine the concentration of a variety of components and/or contaminents in numerous solutions. The impregnation of the Nylon IV is accomplished by first immersing the Nylon IV in the test reagent solution and then removing the moisture content, thus leaving the dry test reagent impregnated in the Nylon IV. When water or a solution to be tested is added to the well the enzymes and other reagent constituents are leached out of the well material, resulting in a working test reagent. Upon completion of the reaction between the test sample and the test reagent, a color is formed and a determination of analyte concentration, based on the intensity of the color, is made by the above-described methods.

In order that the maximum amount of test reagent be absorbed by the nylon, it is necessary to assure that the Nylon IV is in a dry condition prior to impregnation. This will ensure that enough of the enzyme and other reagent constituents will be available upon reconstitution. Due to the nature of the reaction which normally takes place between the enzymes, reagents and test samples, it is permitted that an excess amount of enzyme and/or reagents be present; it is not necessary therefore that the amount of impregnate absorbed in any way be limited.

It has been found that vacuum drying of the Nylon IV material prior to impregnation by immersion aids in absorption. In this regard the time the nylon should be immersed in the test reagent solution varies from about 1 to 90 minutes and preferably between 15 and 60 minutes, depending upon the physical size of the well and the particular impregnate being used. Obviously, the larger the well, the more reagent needed, and therefore, the longer the immersion time. Subsequent to immersion, the Nylon IV material is removed from the solution and dried at room temperature. After drying, the entire apparatus should be stored at temperatures of about 0° to 4° C. to ensure stability of the reagents and enzymes.

During use a pre-measured test sample is placed in the well. This test sample may be diluted with a suitable solvent. Upon introduction of the test sample into the well portion of the apparatus the enzymes and other reagents are leached out of the Nylon IV to form a working test solution; a color change specific to the type of reagents present and the test being performed will result. The intensity of this color, which is measured as previously discussed, can now be used to quantitively calculate the concentration of the particular analyte under consideration.

Although the present invention has been discussed in terms of all the enzymes and/or reagents being impregnated in the well walls, it is to be understood that fewer than all the ingredients may be so impregnated with the remaining constiuents being physically added to the well at the time of testing. Indeed, this subsequent addition is desired in cases where a single enzyme may be utilized for determinating the concentration of a number of different analytes depending upon the particular reagents used in combination with it.

As would be understood by one skilled in the art, the above-described invention lends itself to a number of various tests for both blood and urine analysis; the following are exemplary of these tests.

A commonly used method for the determination of blood urea are the Urease method and those methods utilizing diacetylmonoxyime. In the Urease methods serum is reacted with the enzyme urease releasing ammonia. The ammonia then couples with various reagents, including a chromogen, to form a color, the intensity of which is measured spectrophotometrically.

In the present invention the Nylon IV well is impregnated with a solution comprising the enzyme Urease as well as phenolhypochlorite and any catalyst which may be necessary to complete the reaction. Upon addition of the serum to be tested, the urease enzyme and reagents are leached out of the Nylon IV and the urea present in the serum reacts with the urease. The resulting ammonia reacts with the hypochlorite followed by subsequent coupling with phenol to form a chromogen, indophenol blue. As is known in the art, the color intensity of the resulting color is proportional to the concentration of urea present. The intensity is then measured using the above-described method and apparatus at a radiation of 580 nm to 640 nm and the concentration of urea determined. It is noted that although the above is discussed as a one step process, it may, and often is, accomplished in two steps.

The present invention may also be used for the determination of cholesterol content in human serum. In this embodiment a test reagent comprising lipase, oxidase, activators and phenol is prepared. This solution is then used to impregnate the Nylon IV well. Alternatively, the Nylon IV is impregnated only with the lipase and oxidase and at the time of use the appropriate activators and phenols are placed in the well and the test sample added.

Upon addition of the serum to the well the enzyme and/or test reagents are leached out of the Nylon IV and the test reaction begins. The cholesterol esters are hydrolyzed to free cholesterol and fatty acids by Lipase. The cholesterol is oxidized to cholest-4-en-3-one and hydrogen peroxide in a reaction catalyzed by the cholesterol oxidase (CO). Peroxidase (POD) then catalyzes the reaction between hydrogen peroxide, 4-aminoantipyrine, and phenol to produce a quinoneimine which has an absorbence maximum at 510 nm. The intensity of the color produced is directly proportional to the total cholesterol level in the sample. The intensity is then measured using the above-described method and apparatus and the cholesterol content determined.

A further example of the use of the present invention is the impregnation of the Nylon IV using a combination of reagents for the determination of glucose content in serum plasma or urine. In this embodiment the Nylon IV is impregnated with glucose oxidase, peroxidase, 4-aminoantipyrine and phenol. Alternatively, the Nylon IV may be impregnated using a mixture of glucose oxidase and peroxidase and the 4-aminoantipyrine and phenol added to the well at the time of the test.

Upon introduction of the serum or urine into the well, any glucose present is oxidized in the presence of glucose oxidase to gluconic acid and hydrogen peroxide. Then, in the presence of peroxidase, the hydrogen peroxide reacts with 4-aminoantipyrine and phenol to form a red color. The color intensity is proportional to the concentration of glucose and can be measured photometrically at 510 nm, using the apparatus and methods previously described.

In a further embodiment of the present invention Nylon IV strips are prepared and impregnated with the particular enzymes and reagents necessary to conduct a specific test. For example, in accordance with the previous example a thin non-fibrous Nylon IV strip is impregnated with a solution of peroxidase, glucose oxidase and the necessary reagents to form a red color when glucose is present in the serum or urine. The nylon strip is dried, packaged and stored for any period of time until needed.

Upon introducing the Nylon IV strip into the serum or urine to be tested, the Nylon IV absorbs the test solution, thereby beginning the above described reaction and ultimately forming a color. At that point a visual or instrument evaluation can be made based upon the color intensity of the dye.

It is an important aspect of this embodiment of the present invention that unlike the test strips of the prior art, the present test strips will remain permanently dyed, thus creating a permanent record of the test result. This permanent bonding is due to the unique molecular structure and absorption qualities of the Nylon IV strip. The strips of the prior art, on the other hand, lose their color rapidly, and thus, must be tested or evaluated within a short period of time after the test reaction is complete.

In choosing the particular enzymes and/or reagents for use in conjunction with Nylon IV one should keep in mind that the absorption of these materials is accomplished at the molecular level and it is therefore important to consider their molecular weight and size, since materials having too large a molecular size will not be absorbed by the Nylon IV. For example, various lipids, due to their large molecular size, will not penetrate the Nylon IV structure, whereas analytes, such as glucose or cholesterol, will.

It has been found that the following enzymes are absorbed satisfactorily into the Nylon IV: glucose oxidase, lactate oxidase, pyruvate oxidase, glycerol oxidase, alcohol oxidase, urease, lipase and peroxidase. Similarly, the following chromogens are satisfactorily absorbed: 4-aminoantipyrine, 4-aminophenazone and the tetrazolium salts.

It has also been found that this selective absorption by Nylon IV greatly increases the accuracy of the test results, since it limits the amount of lipemic interference normally encountered when conducting the type of tests previously discussed. Lipemic interference, as would be understood by one skilled in the art, is the interference of large molecular compounds with the interface of the test reagents and the serum components to be tested. Due to the unique properties of the Nylon IV, it has been found that these large molecules are prevented from entering the strip material, and therefore interfering with the interface of the serum components and the test reagents impregnated in the strip.

Although the physical dimensions of the strip may vary widely, one should keep in mind that subsequent evaluation of the strip may require that light pass through it and therefore the thickness should not be so great as to substantially interfere with the light path. It has been found that thicknesses of about 0.25 mm to 2 mm perform satisfactorily in that they absorb sufficient quantities of reagents while still allowing light to pass through for instrumental evaluation subsequent to use.

The present invention has been described in conjunction with preferred embodiments; it is to be understood that modifications and variations may be resorted to without departing from the spirit and scope of the invention as those skilled in the art will readily understand. Such modifications and variations are considered to be within the purview and scope of the invention and the appended claims.

What is claimed is:

1. A test strip for quantitatively determining and permanently recording the concentration of analytes in solution, said test strip comprising a non-fibrous Nylon IV Strip having impregnated therein an enzyme and a plurality of test reagents, said enzyme and test reagents adapted to react with the analyte to produce a color, the intensity of which is indicative of said analyte concentration.

2. The test strip as recited in claim 1, wherein said enzyme is selected from the group consisting of glucose oxidase, lactate oxidase, pyruvate oxidase, glycerol oxidase, alcohol oxidase, urease, lipase and peroxidase.

3. The test strip as recited in claim 1, wherein said reagents are selected from the group consisting of 4-aminoantipyrine, 4-aminophenazone and the tetrazolium salts.

4. The test strip as recited in claim 1, wherein the Nylon IV strip has a thickness of about 0.25 mm to 2 mm.

* * * * *